US012622766B2

(12) United States Patent
Sharma et al.

(10) Patent No.: US 12,622,766 B2
(45) Date of Patent: May 12, 2026

(54) VISUALIZATION OF MEDICAL ENVIRONMENTS WITH PREDETERMINED 3D MODELS

(71) Applicant: Shanghai United Imaging Intelligence Co., Ltd., Shanghai (CN)

(72) Inventors: Abhishek Sharma, Boston, MA (US); Arun Innanje, Lexington, MA (US); Terrence Chen, Lexington, MA (US)

(73) Assignee: Shanghai United Imaging Intelligence Co., Ltd., Shanghai (CN)

( * ) Notice: Subject to any disclaimer, the term of this patent is extended or adjusted under 35 U.S.C. 154(b) by 505 days.

(21) Appl. No.: 18/134,234

(22) Filed: Apr. 13, 2023

(65) Prior Publication Data

US 2024/0341903 A1     Oct. 17, 2024

(51) Int. Cl.
*A61B 90/00* (2016.01)
*A61B 34/10* (2016.01)

(52) U.S. Cl.
CPC .............. *A61B 90/36* (2016.02); *A61B 34/10* (2016.02); *A61B 2034/105* (2016.02); *A61B 2090/365* (2016.02)

(58) Field of Classification Search
None
See application file for complete search history.

(56) References Cited

U.S. PATENT DOCUMENTS

| | | | | |
|---|---|---|---|---|
| 2020/0265104 | A1* | 8/2020 | Belt | ..................... G06F 16/9537 |
| 2024/0021318 | A1* | 1/2024 | Wesolowski | ............ G06T 19/00 |
| 2024/0177326 | A1* | 5/2024 | Karanam | .................. G06T 7/75 |
| 2024/0341903 | A1* | 10/2024 | Sharma | .................. A61B 34/10 |

FOREIGN PATENT DOCUMENTS

| | | |
|---|---|---|
| CN | 101452339 B | 6/2009 |
| CN | 107613897 B | 1/2018 |
| CN | 109792548 B | 5/2019 |

* cited by examiner

*Primary Examiner* — Darryl V Dottin
(74) *Attorney, Agent, or Firm* — Zhong Law, LLC

(57) ABSTRACT

An object or person in a medical environment may be identified based on images of the medical environment. The identification may include determining an identifier associated with the object or the person, a position of the object or the person in the medical environment, and a three-dimensional (3D) shape/pose of the object or the person. Representation information that indicates at least the determined identifier, position in the medical environment, and 3D shape/pose of the object or the person may be generated and then used (e.g., by a visualization device) together with one or more predetermined 3D models to determine a 3D model for the object or the person identified in the medical environment and generate a visual depiction of at least the object or the person in the medical environment based on the determined 3D model and the position of the object or the person in the medical environment.

17 Claims, 8 Drawing Sheets

400

500

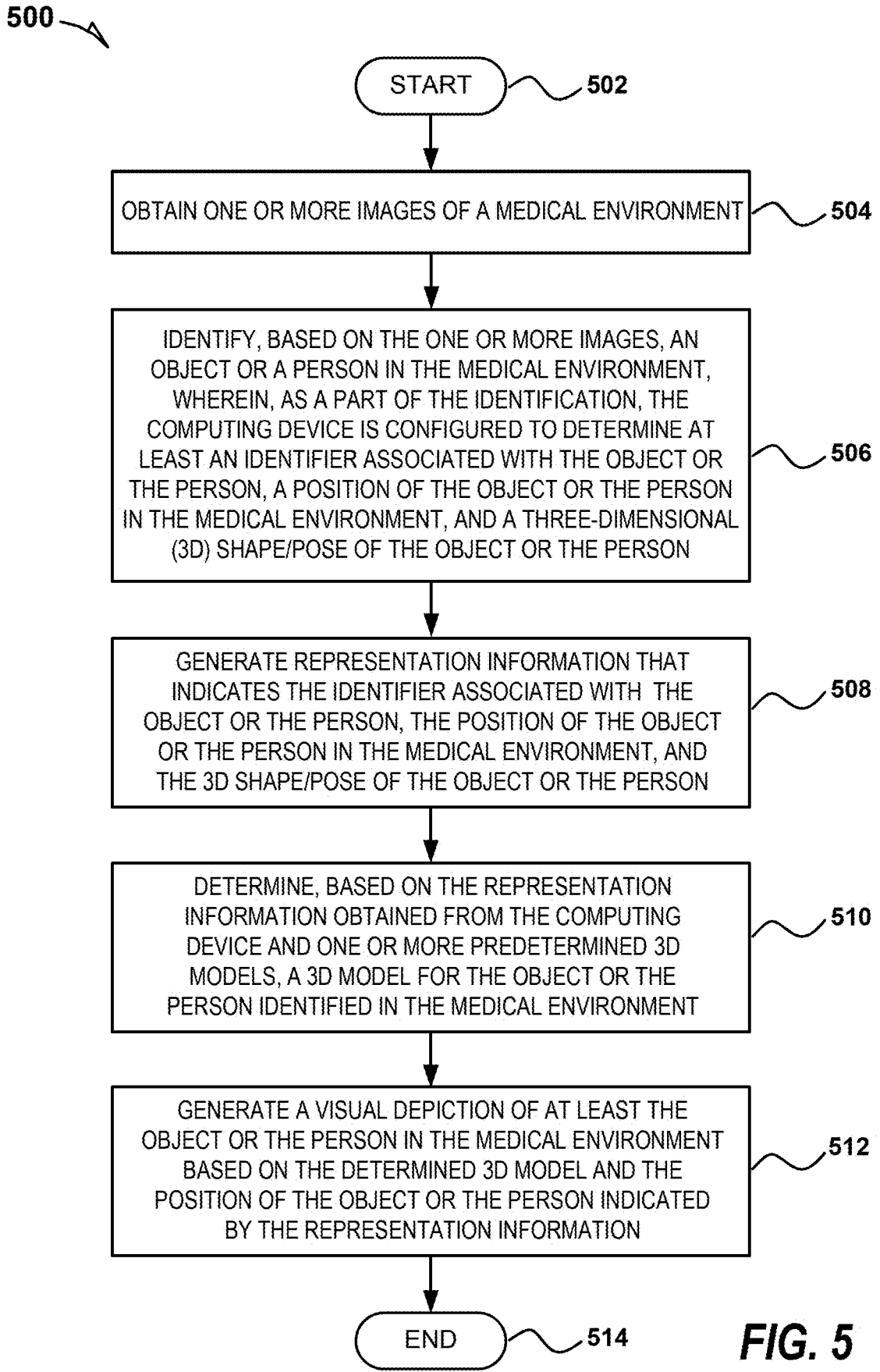

START ⟋502

OBTAIN ONE OR MORE IMAGES OF A MEDICAL ENVIRONMENT ⟋504

IDENTIFY, BASED ON THE ONE OR MORE IMAGES, AN OBJECT OR A PERSON IN THE MEDICAL ENVIRONMENT, WHEREIN, AS A PART OF THE IDENTIFICATION, THE COMPUTING DEVICE IS CONFIGURED TO DETERMINE AT LEAST AN IDENTIFIER ASSOCIATED WITH THE OBJECT OR THE PERSON, A POSITION OF THE OBJECT OR THE PERSON IN THE MEDICAL ENVIRONMENT, AND A THREE-DIMENSIONAL (3D) SHAPE/POSE OF THE OBJECT OR THE PERSON ⟋506

GENERATE REPRESENTATION INFORMATION THAT INDICATES THE IDENTIFIER ASSOCIATED WITH THE OBJECT OR THE PERSON, THE POSITION OF THE OBJECT OR THE PERSON IN THE MEDICAL ENVIRONMENT, AND THE 3D SHAPE/POSE OF THE OBJECT OR THE PERSON ⟋508

DETERMINE, BASED ON THE REPRESENTATION INFORMATION OBTAINED FROM THE COMPUTING DEVICE AND ONE OR MORE PREDETERMINED 3D MODELS, A 3D MODEL FOR THE OBJECT OR THE PERSON IDENTIFIED IN THE MEDICAL ENVIRONMENT ⟋510

GENERATE A VISUAL DEPICTION OF AT LEAST THE OBJECT OR THE PERSON IN THE MEDICAL ENVIRONMENT BASED ON THE DETERMINED 3D MODEL AND THE POSITION OF THE OBJECT OR THE PERSON INDICATED BY THE REPRESENTATION INFORMATION ⟋512

END ⟋514

FIG. 5

VISUALIZATION OF MEDICAL ENVIRONMENTS WITH PREDETERMINED 3D MODELS

BACKGROUND

The popularity of visualization devices such as virtual reality (VR) devices and augmented reality (AR) devices together with the creation of a shared, immersive, persistent, three-dimensional (3D) virtual space (e.g., a metaverse) may greatly enhance the ways in which humans can interact with each other in many areas of life. For example, in the healthcare field, doctors can use the metaverse and VR/AR devices to create 3D clinical applications, to make a patient's experience more interactive, to monitor a patient's vital signs in a virtual environment, etc. Complex healthcare activities, such as a medical operation requiring surgery, may be aided by a virtual representation of an operating room that is very realistic (e.g., in a VR/AR space). A high degree of realism in a virtual environment may be achieved by streaming the environment information in real time to a visualization application (e.g., the app may be associated with a pair of VR glasses or any other connected computing device) in order to give the operating doctors and technicians the confidence and feeling of completeness while using the visualization application for surgical planning or even during the surgery. However, trying to stream a large amount of 3D data from multiple sensing devices, such as cameras, that may be installed in a medical environment to the visualization application may create a bandwidth bottleneck even with the use of data compression methods and high speed communication networks (e.g., 5G networks) to reduce the bandwidth requirements.

SUMMARY

Described herein are systems, methods and instrumentalities associated with generating a visualization of an object or a person within a medical environment based on predetermined 3D models. A system as described herein may comprise a computing device configured to obtain one or more images of a medical environment (e.g., from sensing devices in the medical environment as described below) and identify, based on the one or more images, an object or a person in the medical environment, wherein, as a part of the identification, the computing device may be configured to determine at least an identifier associated with the object or the person, a position of the object or the person in the medical environment, and a three-dimensional (3D) shape of the object or the person. The computing device may further be configured to generate representation information that indicates at least the identifier associated with the object or the person, the position of the object or the person in the medical environment, and the 3D shape of the object or the person. The system may also include a visualization device (e.g., a virtual reality headset or a personal computing device) configured to obtain the representation information generated by the computing device and determine, based on the representation information obtained from the computing device and one or more predetermined 3D models, a 3D model for the object or the person identified in the medical environment. The visualization device may be further configured to generate a visual depiction of at least the object or the person in the medical environment based on the determined 3D model and the position of the object or the person indicated by the representation information.

In some embodiments, the one or more predetermined 3D models may be associated with respective model identifiers and the visualization device may be configured to determine the 3D model for the object or the person based on determining a candidate 3D model for the object or the person by matching the identifier associated with the object or the person with the model identifier associated with the candidate 3D model. In some embodiments, the visualization device may be configured to determine the 3D model for the object or the person by modifying the candidate 3D model based at least on the 3D shape of the object or the person indicated by the representation information.

In some embodiments, the computing device may be further configured to determine a 3D pose of the object or the person based on the one or more images, wherein the representation information further indicates the 3D pose of the object or the person, and wherein the visualization device is configured to modify the candidate 3D model further based on the 3D pose of the object or the person to obtain the 3D model for the object or the person.

In some embodiments, the visualization device may be configured to determine that none of the one or more predetermined 3D models matches the object or the person and to generate the 3D model for the object or the person based on the 3D shape and 3D pose of the object or the person indicated by the representation information.

In some embodiments, the one or more predetermined 3D models may include one or more 3D object models associated with a medical device in the medical environment and the one or more predetermined 3D models may further include one or more 3D human models associated with a medical professional or a patient in the medical environment. In some embodiments, the one or more predetermined 3D models may include one or more computer-aided design (CAD) models or one or more mesh models. In some embodiments, the one or more predetermined 3D models may be stored in a database accessible to at least one of the computing device or the visualization device.

In some embodiments, the one or more predetermined 3D models may be associated with respective model identifiers that indicate respective classifications of the one or more predetermined 3D models. Furthermore, the computing device may be configured to determine a classification for the object or the person based on the one or more images, matching the classification to a candidate model stored in the database, and use the model identifier of the candidate model as the identifier of the object or the person.

In some embodiments, the computing device may be configured to identify the object or the person in the medical environment by detecting the object or the person in the one or more images based on a machine learning model pre-trained for object or human detection. In some embodiments, the computing device may be configured to identify the object or the person in the medical environment by determining at least the 3D shape of the object or the person based on a machine learning model pre-trained for 3D object or human shape estimation.

In some embodiments, the system may further comprise at least one image sensor configured to be installed in the medical environment and the computing device may be configured to obtain the one or more images of the medical environment from the at least one image sensor.

BRIEF DESCRIPTION OF THE DRAWINGS

A more detailed understanding of the examples disclosed herein may be had from the following description, given by way of example in conjunction with the accompanying drawing.

FIG. 5 shows a flow diagram illustrating an example method for generating a visualization of an object or a person detected within a medical environment based on predetermined 3D models in accordance with one or more embodiments described herein.

DETAILED DESCRIPTION

The present disclosure is illustrated by way of example, and not by way of limitation, in the figures of the accompanying drawings.

Figure 1:
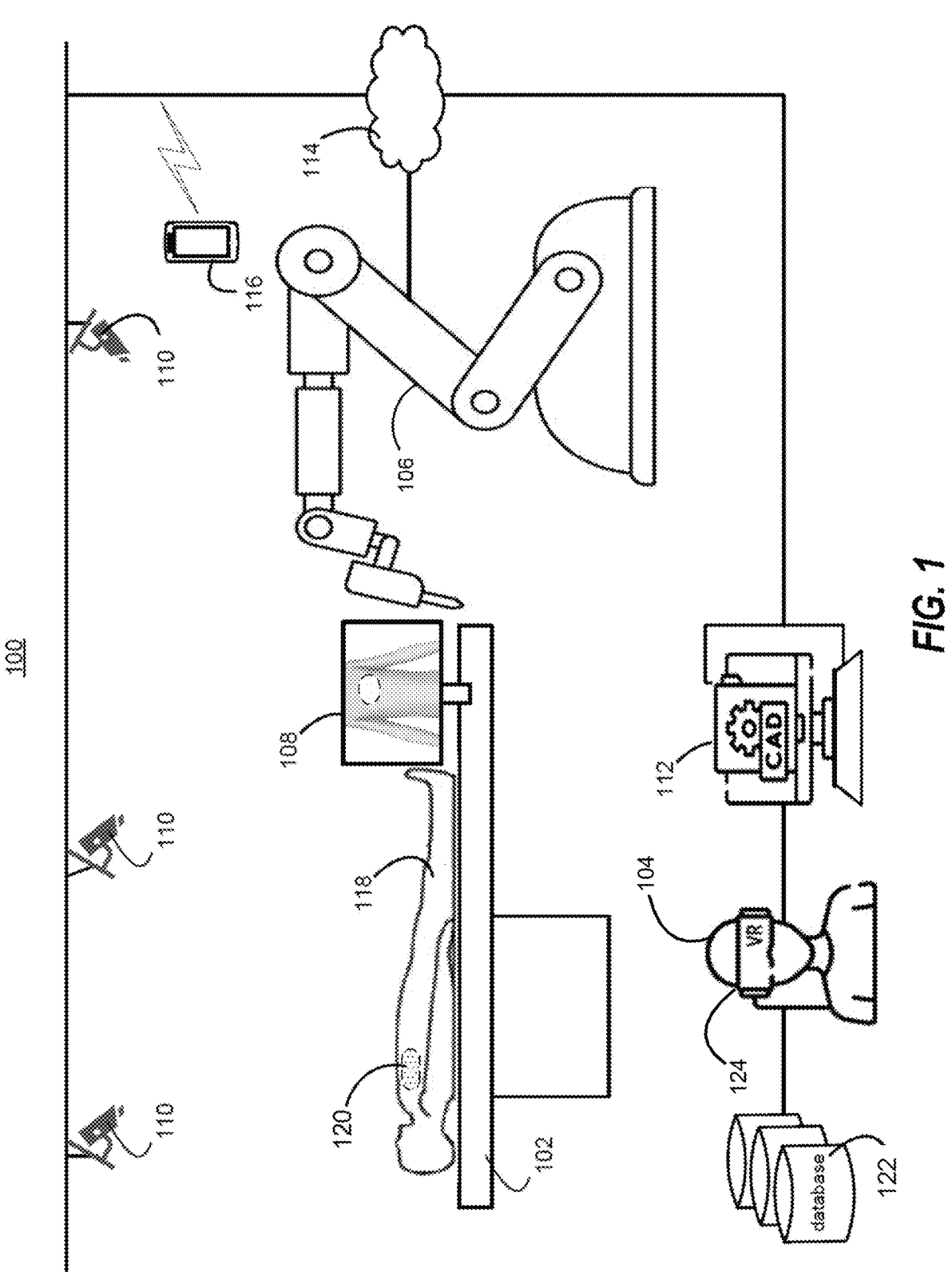
FIG. 1 shows a diagram illustrating an example system that may be used for generating a visualization of a medical environment based on predetermined 3D models in accordance with one or more embodiments described herein.

FIG. 1 is a diagram illustrating an example system that may be used for generating a visualization of a medical environment 100 (including at least an object or a person) based on predetermined 3D models in accordance with one or more embodiments described herein.

The medical environment 100 may be any facility in a healthcare setting including. e.g., an operating room or a scan room at a hospital, a rehabilitation facility, a fitness center, etc. The medical environment 100 may be equipped with various tools, devices, and/or equipment such as a patient bed 102, a surgical robotic arm 106, a patient monitoring device 108, etc. The tools, devices, and/or equipment may be maneuvered (e.g., manually or automatically) to accommodate the needs of a medical procedure being performed on a patient 118 in the medical environment 100. For example, the patient bed 102 may be raised or lowered, the surgical robotic arm 106 may be manipulated (e.g., moved, tilted, or rotated) towards a specific location (e.g., towards the patient 118), a lighting device (not shown) may be adjusted to focus on a surgical site, etc.

Part or all of the operations in the medical environment 100 may be automated, for example, utilizing one or more sensing devices 110 and/or a processing device 112 (e.g., a computer) communicatively coupled to the one or more sensing devices 110. The sensing devices 110 may be installed at various locations of the medical environment 100 and may be communicatively coupled to the processing device 112 and/or other devices of the medical environment 100 via a communication network 114. Each of the sensing devices 110 may include one or more sensors such as one or more 2D visual sensors (e.g., 2D cameras), one or more 3D visual sensors (e.g., 3D cameras), one or more red, green and blue (RGB) sensors, one or more depth sensors, one or more RGB plus depth (RGB-D) sensors, one or more thermal sensors (e.g., infrared (FIR) or near-infrared (NIR) sensors), one or more motion sensors, one or more radar sensors, and/or other types of image capturing circuitry that are configured to capture images of a person or an object in the medical environment 100. Depending on the type of cameras, sensors, and/or image capturing circuitry included in the sensing devices 110, the images generated by the sensing devices 110 may include, for example, one or more photos, one or more thermal images, one or more radar images, and/or the like. The sensing devices 110 may be configured to generate the images described herein in response to detecting a person (e.g., patient 118) or an object (e.g., surgical robotic arm 106) in the medical environment 100. The sensing devices 110 may also be configured to generate the images described herein based on a preconfigured schedule or time interval, or upon receiving a control signal (e.g., from a remote control device or from processing device 112) that triggers the image generation.

Each of the sensing devices 110 may include a functional unit (e.g., a processor) configured to control the image capturing functionalities described herein. The functional unit may also be configured to process the images (e.g., pre-process the images before sending the images to another processing device), communicate with other devices located inside or outside of the medical environment 100, determine a characteristic (e.g., a person or object) of the medical environment 100 based on the captured images, etc. Each of the sensing devices 110 may include a communication circuit and may be configured to exchange information with one or more other sensing devices via the communication circuit and/or the communication network 114. The sensing devices 110 may form a sensor network within which the sensing devices 110 may transmit data to and receive data from each other. The data exchanged between the sensing devices 110 may include, for example, imagery data captured by each sensing device 110 and/or control data for discovering each sensing device's 110 presence and/or calibrating each sensing device's 110 parameters. For instance, when a new sensing device 110 is added to the medical environment 100, the sensing device 110 may transmit messages (e.g., via broadcast, groupcast or unicast) to one or more other sensing devices 110 in the sensor network and/or a controller (e.g., a processing device as described herein) of the sensor network to announce the addition of the new sensing device 110. Responsive to such an announcement or transmission of data, the other sensing devices 110 and/or the controller may register the new sensing device 110 and begin exchanging data with the new sensing device 110.

The sensing devices 110 may be configured to be installed at various locations of the medical environment 100 including, e.g., on a ceiling, above a doorway, on a wall, on a medical device, etc. From these locations, each of the sensing devices 110 may capture images of a person or an object that is in the field of view (FOV) of the sensing device 110 (e.g., the FOV may be defined by a viewpoint and/or a viewing angle). The FOV of each of the sensing devices 110 may be adjusted manually or automatically (e.g., by transmitting a control signal to the sensing device) so that the sensing device 110 may take images of a person or an object in the medical environment 100 from different viewpoints or different viewing angles.

Each of the sensing devices 110 may be configured to exchange information with other devices (e.g., surgical robotic arm 106) in the medical environment 100, e.g., via the communication network 114. In examples, each of the sensing devices 110 may be configured to transmit the images captured by the sensing device 110 to the processing device 112. In examples, the processing device 112 may be configured to retrieve the images captured by the sensing devices 110 from the sensing devices 110, e.g., via a pull mechanism. The transmission and/or retrieval of images may be performed on a periodic basis or in response to receiving a control signal instructing the transmission or retrieval. For instance, the processing device 112 may be configured to receive a notification from the sensing devices 110 when images are captured and retrieve the image in response to receiving the notification.

The configuration and/or operation of the sensing devices 110 may be at least partially controlled by a programming device 116. For example, the programming device 116 may be configured to initialize and modify one or more operating parameters of the sensing devices 110 including, e.g., the resolution of images captured by the sensing devices 110, a periodicity of data exchange between the sensing devices 110 and the processing device 112, a frame or bit rate associated with the data exchange, a duration of data storage on the sensing devices, etc. The programming device 116 may also be configured to control one or more aspects of the operation of the sensing devices 110 such as triggering a calibration of the sensing devices 110, adjusting the respective orientations of the sensing devices 110, zooming in or zooming out on a person or object in the medical environment 100, triggering a reset, etc. The programming device 116 may be a mobile device (e.g., such a smartphone, a tablet, or a wearable device), a desktop computer, a laptop computer, etc., and may be configured to communicate with the sensing devices 110 and/or the processing device 110 over the communication network 114. The programming device 116 may receive information and/or instructions from a user (e.g., via a user interface implemented on the programming device 116) and forward the received information and/or instructions to the sensing devices 110 via the communication network 114.

The communication network 114 described herein may be a wired or a wireless network, or a combination thereof. For example, the communication network 114 may be established over a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) or 5G network), a frame relay network, a virtual private network (VPN), a satellite network, and/or a telephone network. The communication network 114 may include one or more network access points. For example, the communication network 114 may include wired and/or wireless network access points such as base stations and/or internet exchange points through which one or more devices in the medical environment 100 may be connected to exchange data and/or other information. Such exchange may utilize routers, hubs, switches, server computers, and/or any combination thereof.

The processing device 112 may be configured to receive images from the sensing devices 110 and determine one or more characteristics of the medical environment 100 based on the images. These characteristics may include, for example, people and/or objects that are present in the medical environment 100 and the respective positions of the people and/or objects in the medical environment 100. The people present in the medical environment 100 may include, e.g., a patient 118 and/or medical staff (e.g., the doctor 104, a technician, a nurse, etc.) attending to the patient 118. The objects present in the medical environment 100 may include, e.g., the surgical robotic arm 106, the monitoring device 108, the patient bed 102, and/or other medical devices or tools not shown in FIG. 1. The position of the object or the person may include a 3D position (e.g., in terms of the [X, Y, Z] coordinates) of the object or the person within a 3D layout of the medical environment 100.

In examples, a system for generating a visualization of an object or a person detected within the medical environment 100 based on predetermined 3D models may include a computing device (e.g., sensing device 110 or processing device 112) configured to obtain one or more images of the medical environment 100 (e.g., using one or more image sensors of the sensing devices 110 in the medical environment 100) and identify, based on the one or more images, an object (e.g., robotic arm 106) or a person (e.g., patient 118) in the medical environment 100, wherein, as a part of the identification, the computing device may be configured to determine at least an identifier (e.g., a model identifier or model ID) associated with the object or the person, a location or position (e.g., 3D coordinates) of the object or the person in the medical environment 100, a 3D pose (e.g., orientation) of the object or the person, and/or a 3D shape of the object or the person (e.g., the body shape of the person or the size of the object, etc.). The computing device may further be configured to generate representation information that indicates at least the identifier associated with the object or the person (e.g., a model ID for the object or the person), the location or position of the object or the person in the medical environment, the 3D pose of the object or the person, and/or the 3D shape of the object or the person. The visualization system may also include a visualization device 124 (e.g., the VR goggles worn by doctor 104 or some other person not in medical environment 100, a computing device with a display located remoted from medical environment 100, etc.) configured to obtain the representation information generated by the computing device and determine, based on the representation information obtained from the computing device and one or more predetermined 3D models (e.g., stored in database 122 as described below), a 3D model for the object or the person identified in the medical environment 100. The visualization device may be further configured to generate a visual depiction of at least the object or the person in the medical environment 100 based on the determined 3D model and the position of the object or the person in the medical environment 100 as indicated by the representation information.

As noted above, the visualization device 124 may be communicatively coupled to a database 122 (and/or the processing device 112), for example, via the communication network 114. The database 122 may comprise a patient or medical environment record repository that may be configured to store basic information of the patient 118, diagnostic and/or treatment histories of the patient 118, scan images of the patient 118, etc., as well as predetermined 3D models for objects and/or people commonly seen in the medical environment 100. As a part of the generation of the visualization of the object or the person in the medical environment 100, the visualization device 124 may be configured to retrieve a predetermined 3D model of the object or the person that may be stored in database 122. The 3D models may be created beforehand for many objects (e.g., medical equipment such as surgical arm 106) and people (e.g., a patient 118 and medical personnel such as doctor 104) that may be present in the medical environment 100. For example, the predetermined 3D models may be part of a database of computer-aided design (CAD) models stored in database 122. Accordingly, after running an object/person detection algorithm on the 3D data or 2D data collected from the multiple sensing devices 110 in the medical environment 100, the processing device 112 may create the representation data described above based on the detected objects/persons and their respective identifiers, their respective positions in the medical environment 100, and their respective 3D poses and/or shapes. The size of the representation data may be smaller than the size of 3D models that may have to be generated and/or transmitted if the processing device 112 or sensing device 110 were to be tasked with constructing the 3D models for the person or object in the medical environment 100. As such, by sending the representation data from the processing device 112 (or the sensing device 110) to the visualization device 124, and having the visualization device 124 determine the 3D model for the object or the person based on the representation data and the predetermined 3D models from the database 122, computation and/or communication resources may be saved for the sensing device 110 and/or processing device 112.

The visualization device 124 may be configured to display, for example, the determined 3D model of the patient 118 on a display device so that the 3D model may be viewed or interacted with by medical personnel remotely located from the medical environment 100. For example, the doctor 104 may not be in medical environment 100 while still controlling robotic arm 106 during a medical procedure associated with an anatomical structure 120 (e.g., the heart) indicated on the created 3D model for patient 118.

In examples, the one or more predetermined 3D models (e.g., CAD model stored in database 122) may be associated with respective model identifiers and the visualization device 124 (e.g., VR goggles worn by doctor 104) may be configured to determine the 3D model for the object or the person by matching the identifier of the object or the person, as indicated by the representation information, with the model identifier of a candidate predetermined 3D model in the database 122 (e.g., a CAD model from the database 122). In examples, the visualization device 124 (e.g., VR goggles worn by doctor 104) may be configured to modify the candidate predetermined 3D model (e.g., which may be a generic model for the object or the person) based at least on the 3D shape and/or pose of the object or the person, as indicated by the representation information, in order to obtain the 3D model for the object or the person.

In examples, the visualization device 124 (e.g., VR goggles worn by doctor 104) may be configured to determine the 3D model for the object or the person identified in the medical environment 100 based on determining that none of the one or more predetermined 3D models (e.g., in the database 122) matches the object or the person, in which case the visualization device 124 may be configured to determine the 3D model for the object or the person based on the 3D shape and the 3D pose of the object or the person indicated by the representation information.

As noted above, the one or more predetermined 3D models (e.g., in the database 122) may include one or more 3D object models associated with medical devices (e.g., the robotic arm 106) in the medical environment 100 and the one or more predetermined 3D models may further include one or more 3D human models associated with a medical professional (e.g., the doctor 104) or a patient (e.g., the patient 118) in the medical environment 100. Also as noted above, the one or more predetermined 3D models may include one or more computer-aided design (CAD) models or one or more mesh models. Also as noted above, the database 122 may be accessible to at least one of the computing device of the visualization system (e.g., processing device 112) or the visualization device 124 (e.g., VR goggles worn by doctor 104) of the visualization system.

In examples, the one or more predetermined 3D models stored in the database 122 may be associated with respective model identifiers (e.g., model IDs such as "1" for a patient bed, "2" for a surgical robot, "3" for a surgeon, etc.), and the computing device (e.g., processing device 112) of the visualization system may have access to the model ID information, for example, via direct access to the database 122 or based on a local copy of the model IDs possessed by the computing device. The computing device may be further configured to classify the object or the person detected in the medical environment 100 (e.g., a patient bed, a surgical robot, a surgeon, etc.) based on the one or more images collected by the sensing devices 110, and associate the object or the person with a corresponding model ID based on the classification (e.g., model IDs such as "1" for a patient bed, "2" for a surgical robot, "3" for a surgeon, etc.). The computing device may be configured to detect and classify the object or the person in the medical environment 100 based on a machine learning model pre-trained for object or human detection and classification. The computing device may be further configured to determine at least the 3D pose and/or 3D shape of the object or the person based on a machine learning model pre-trained for 3D object or human pose/shape estimation.

As noted above, the system for generating a visualization of an object or a person within a medical environment 100 may include at least one image sensor (e.g., sensing devices 110) configured to be installed in the medical environment 100, wherein the computing device (e.g., processing device 112) may be configured to obtain the one or more images of the medical environment 100 from the at least one image sensor.

In the examples, one or more of the tasks are described as being initiated and/or implemented by a computing device, such as the processing device 112, in a centralized manner. It should be noted, however, that the tasks may also be distributed among multiple processing devices (e.g., interconnected via the communication network 114, arranged in a cloud-computing environment, etc.) and performed in a distributed manner. Further, even though the processing device 112 has been described herein as a device separate from the sensing devices 110, the functionalities of the processing device 112 may be realized via one or more of the sensing devices (e.g., the one or more sensing devices 110 may comprise respective processors configured to perform the functions of the processing device 112 described herein). Therefore, in some implementations, a separate processing device 112 may not be included and one or more of the sensing devices 110 may assume the responsibilities of the processing device.

Figure 2:
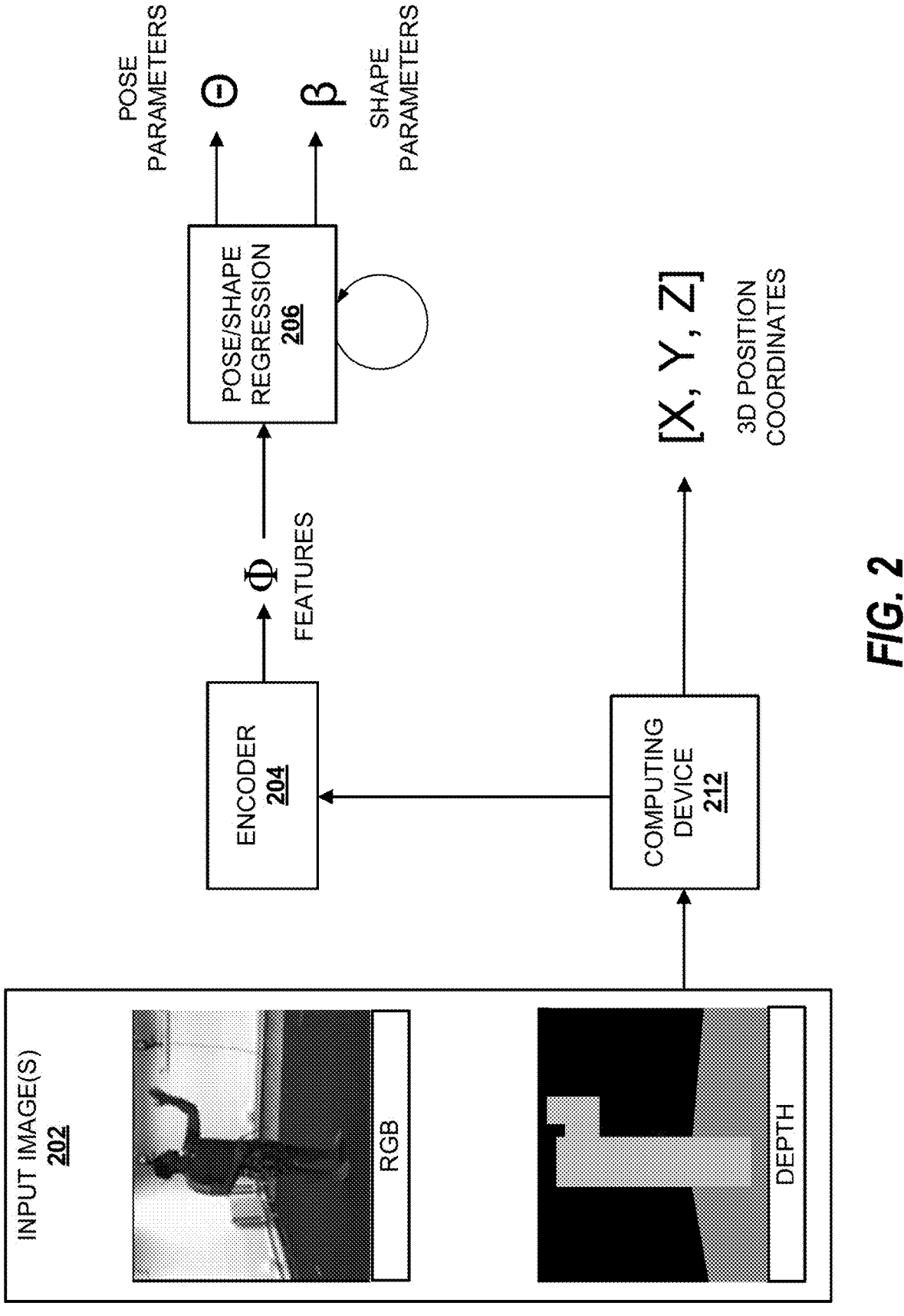
FIG. 2 shows a simplified block diagram illustrating how representation information regarding a person in a medical environment may be recovered based on input images of the person in accordance with one or more embodiments described herein.

FIG. 2 shows a simplified block diagram illustrating how representation information regarding a person in a medical environment may be recovered based on input images of the person in accordance with one or more embodiments described herein.

As an initial matter, it should be noted that the process described herein for a person (e.g., patient 118) with respect to FIG. 2 is equally applicable to an object (e.g., robotic arm 106) detected in the medical environment 100. Input images 202 of the person (e.g., RGB and depth images captured by sensing devices 110 in medical environment 100) may be received by a computing device 212 (e.g., processing device 112) and a plurality of features, @, may be extracted from the images, for example, using a pre-trained machine learning (ML) model (e.g., an encoder module 204 of the computing device 212). The extracted features may be provided to a pose/shape regression module 206 (e.g., as a part of the computing device 212), which may be configured to infer parameters and/or 3D coordinates from the extracted features for recovering the representation information. The inferred parameters may include, for example, one or more 3D pose parameters, O, and one or more 3D shape parameters, B, that may respectively indicate the 3D pose and 3D shape of the person's body (or those of an object). Furthermore, the computing device 212 may determine position information regarding the person in the medical environment 100 based on the RGB and/or depth images 202 by, for example, using a triangulation technique to determine the (X, Y, Z) coordinates of the person (or object) in the medical environment 100 based on the camera/depth sensor parameters of the sensing devices 110.

The encoder module 204 and/or the pose/shape regression module 206 may be implemented through one or more neural networks such as one or more convolutional neural networks (CNNs) and/or one or more deep neural networks (DNNs). Each of the one or more neural networks may comprise multiple layers such as an input layer, one or more convolutional layers, one or more non-linear activation layers, one or more pooling layers, one or more fully connected layers, and/or an output layer. Each of the layers may correspond to a plurality of filters (e.g., kernels) and each filter may be designed to detect (e.g., learn) a set of keypoints that collectively represent a respective pattern or feature Φ. The filters may be associated with respective weights that, when applied to an input, produce an output indicating whether certain visual patterns or features Φ have been detected. The weights associated with the filters may be learned by the neural networks through a training process that comprises inputting a large number of images from one or more training datasets to the neural networks, calculating differences or losses resulting from the weights currently assigned to the filters (e.g., based on an objective function such as mean squared error or L1 norm, a margin based loss function, etc.), and updating the weights assigned to the filters so as to minimize the differences or losses (e.g., based on stochastic gradient descent). Once trained (e.g., having learned to recognize patterns or features Φ in the training images), the neural networks may take an image 202 at the input layer, extract and/or classify visual patterns or features Φ from the image 202, and provide an indication at the output layer for an identified pattern or feature Φ or an associated feature class. The identified pattern or feature Φ may be indicated, for example, with a feature descriptor or feature vector.

The one or more neural networks may also be trained to infer, e.g., based on features extracted from the input images 202, 3D pose parameters Θ and 3D shape parameters β associated with the person (or trained similarly for an object). For example, the one or more neural networks may be trained to determine, based on datasets that cover a wide range of human subjects, human activities, background noises, shape and/or pose variations, camera motions, etc., the joint angles of a plurality of joints of a person as depicted in an input image 202. The plurality of joints may include, for example, 23 joints comprised in a skeletal rig as well as a root joint, and the 3D pose parameters Θ derived thereof may include 72 parameters (e.g., 3 parameters for each of the 23 joints and 3 parameters for the root joint, with each parameter corresponding to an axis-angle rotation from a root orientation). The neural networks may also determine, based on the training datasets, one or more 3D shape parameters B for predicting a 3D shape of a person based on the input images 202 of the person. For example, the neural networks may learn to determine the 3D shape parameters β by conducting principle component analysis (PCA) and the 3D shape parameters β thus determined may include a plurality of coefficients (e.g., the first 10 coefficients) of the PCA space.

In examples, to enable a visualization device (e.g., the visualization device 124 of FIG. 1) to select a candidate predetermined 3D model for the person (e.g., the patient 118) from the predetermined 3D models stored in database 122, the computing device 212 may be configured to determine a classification (e.g., a male or female, a patient or a doctor, etc.) for the person based on the one or more input images 202 and/or further determine an identifier (e.g., a model ID) for the person based on the classification. In this way, once the identifier of the person is passed to the visualization device (e.g., indicated by the representation information described herein), the visualization device may select a candidate model for the person from the one or more predetermined 3D models stored in the database 122, for example, by matching the identifier of the person with an identifier (e.g., model ID) of the candidate model.

The computing device 212 may be configured to generate representation data that indicates the information determined using the techniques described above. For example, the representation data may include one or more of the identifier (e.g., model ID) of the person determined by the computing device 212, the position of the person in the medical environment, the pose parameters Θ determined for the person, and/or the shape parameters β determined for the person.

Figure 3:
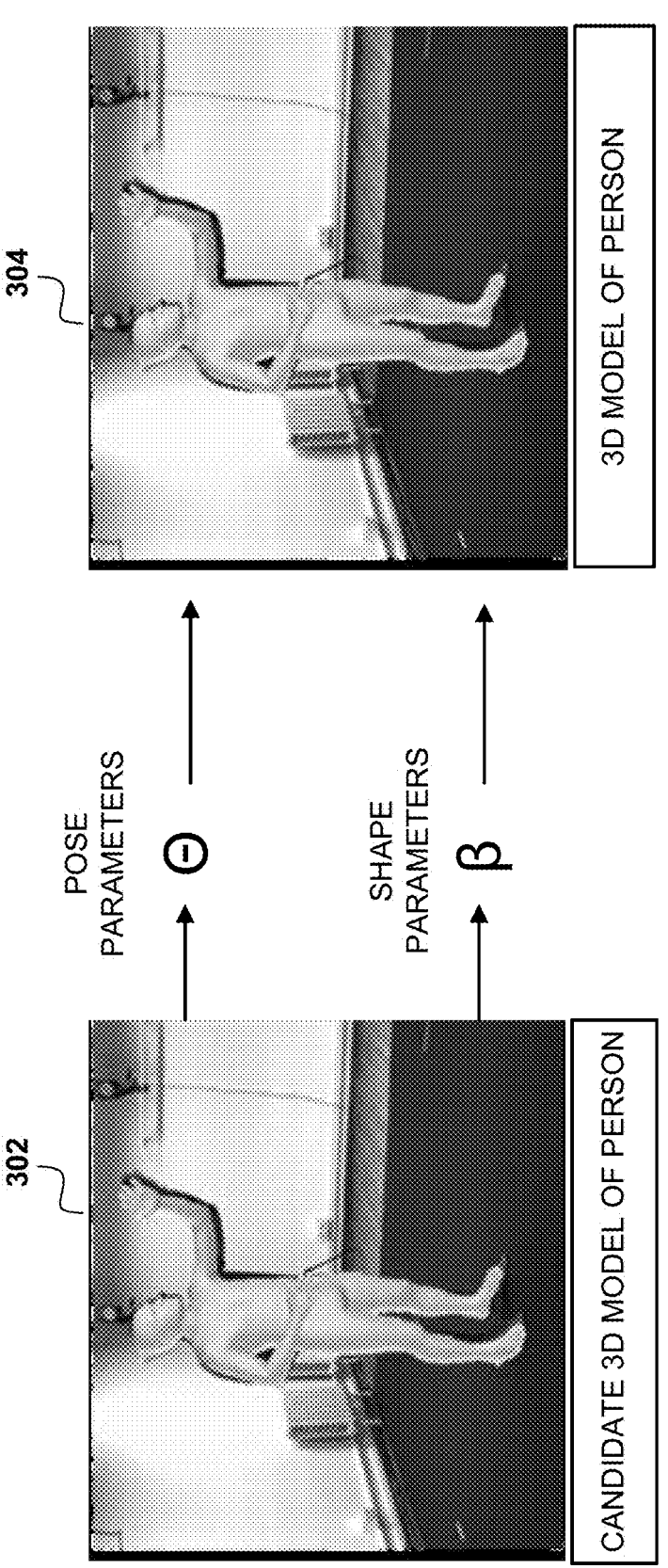
FIG. 3 shows a simplified diagram for modifying a candidate predetermined 3D model based on the 3D shape and/or 3D pose of an object or person, as indicated by the representation information of the object or the person, in order to obtain a 3D model for the object or the person in accordance with one or more embodiments described herein.

FIG. 3 shows a simplified diagram illustrating an example of modifying a candidate predetermined 3D model based on the 3D shape and 3D pose of an object or person, as indicated by the representation information described herein, in order to obtain a 3D model for the object or the person in accordance with one or more embodiments described herein.

As discussed above with respect to FIG. 2, a candidate model 302 may be selected for the person from the one or more predetermined 3D models stored in the database 122. The visualization device (e.g., VR goggles worn by doctor 104) may be configured to determine the 3D model 304 for the person (e.g., the patient 118) or for an object (e.g., the robotic arm 106) by determining, from the predetermined 3D models stored in the database, a candidate predetermined 3D model 302 for the person or the object (e.g., based on ID matching or classification matching) and modifying the candidate predetermined 3D model 302 (e.g., if necessary) based at least on the 3D shape and/or 3D pose of the person, as indicated by the shape and/or pose parameters in the representation information, in order to obtain the 3D model 304 for the person. For example, the candidate predetermine 3D model 302 retrieved from the database may be a parametric model representing the shape and pose of an average person (e.g., a patient or a doctor) or a generic object (e.g., a patient bed, a surgical robot, etc.), and the visualization device may modify the candidate predetermine 3D model by applying the shape and/or pose parameters determined and provided by the computing device (e.g., via the representation information) to the parametric model.

Figure 4:
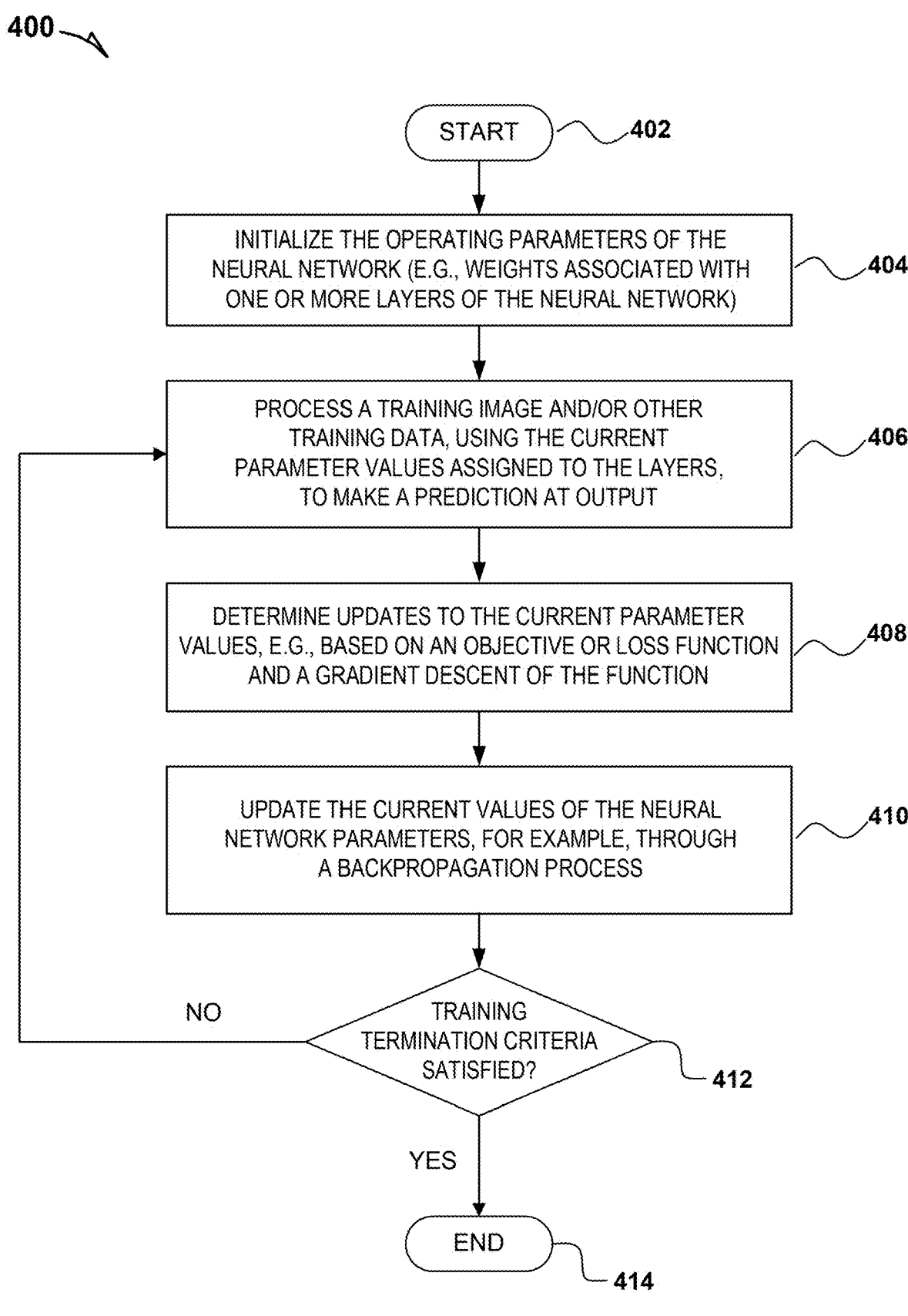
FIG. 4 shows a flow diagram illustrating an example method that may be associated with the training of a neural network in accordance with one or more embodiments described herein.

FIG. 4 shows a flow diagram illustrating an example method 400 for training a neural network to perform one or more of the tasks described herein. The method 400 may be performed using a system of one or more computers. For example, the system may start the training at 402 and, at 404, the system may initialize the operating parameters of the neural network (e.g., weights associated with one or more layers of the neural network), for example, based on samples from one or more probability distributions or parameter values of another neural network with a similar architecture. At 406, the system may use the neural network to process a training image (e.g., depicting an object and/or a person) and/or other training data using the current parameter values assigned to the layers of the neural network. A prediction may be made as a result of the processing and at 408, the system may determine updates to the current parameter values of the neural network, e.g., based on an objective or loss function and a gradient descent of the function. As described herein, the objective function may be designed to minimize the difference between the prediction and a ground truth. The objective function may be implemented using, for example, mean squared error, L1 norm, etc. At 410, the system may update the current values of the neural network parameters, for example, through a backpropagation process. At 412, the system may determine whether one or more training termination criteria are satisfied. For example, the system may determine that the training termination criteria are satisfied if the system has completed a pre-determined number of training iterations, or if the change in the value of the loss function between two training iterations falls below a predetermined threshold. If the determination at 412 is that the training termination criteria are not satisfied, the system may return to 406. If the determination at 412 is that the training termination criteria are satisfied, the system may end the training process 400 at 414.

For simplicity of explanation, the training steps are depicted and described herein with a specific order. It should be appreciated, however, that the training operations may occur in various orders, concurrently, and/or with other operations not presented or described herein. Furthermore, it should be noted that not all operations that may be included in the training process are depicted and described herein, and not all illustrated operations are required to be performed.

FIG. 5 shows a flow diagram illustrating an example method for generating a visualization of a medical environment comprising an object or a person based on one or more images of the medical environment and predetermined 3D models in accordance with one or more embodiments described herein.

The operations of method 500 may start at 502 and then at operation 504, images 202 of the medical environment may be obtained by a computing device, for example, from one or more sensing devices (e.g., which have been installed in the medical environment). At operation 506, the computing device may identify, based on the one or more input images, an object (e.g., robotic arm 106 of FIG. 1) or a person (e.g., patient 118 of FIG. 1) in the medical environment, wherein, as a part of the identification, the computing device may be configured to determine at least an identifier associated with the object or the person, a position of the object or the person in the medical environment, a 3D pose of the object or the person, and/or a 3D shape of the object or the person. At operation 508, the computing device may generate representation information that indicates at least the identifier associated with the object or the person, the position of the object or the person in the medical environment, the 3D pose of the object or the person, and/or the 3D shape of the object or the person. At operation 510, a visualization device (e.g., the VR goggles worn by doctor 104 or by some other person not in the medical environment, as shown in FIG. 1) may obtain the representation information generated by the computing device and determine, based on the representation information obtained from the computing device and one or more predetermined 3D models (e.g., stored on the computing device or obtained from database 122 as described above), a 3D model for the object or the person identified in the medical environment. At operation 512, the visualization device may generate a visual depiction of at least the object or the person in the medical environment based on the determined 3D model and the position of the object or the person in the medical environment as indicated by the representation information.

The computing device (e.g., processing device 112) and the visualization device (e.g., the VR goggles worn by doctor 104) may continuously perform the operations of 502-512, for example, periodically as the visual representation of the person or object in the medical environment is streamed in real time and/or based on new objects and/or persons being detected in the medical environment. At operation 514, the computing device/visualization device may cease performing these operations (e.g., entering an idle state) and end method 500, for example, if no activities are detected in the medical environment and/or if the computing device/visualization device receives a command to cease the operations (e.g., from the doctor 104).

Figures 6A, 6B:
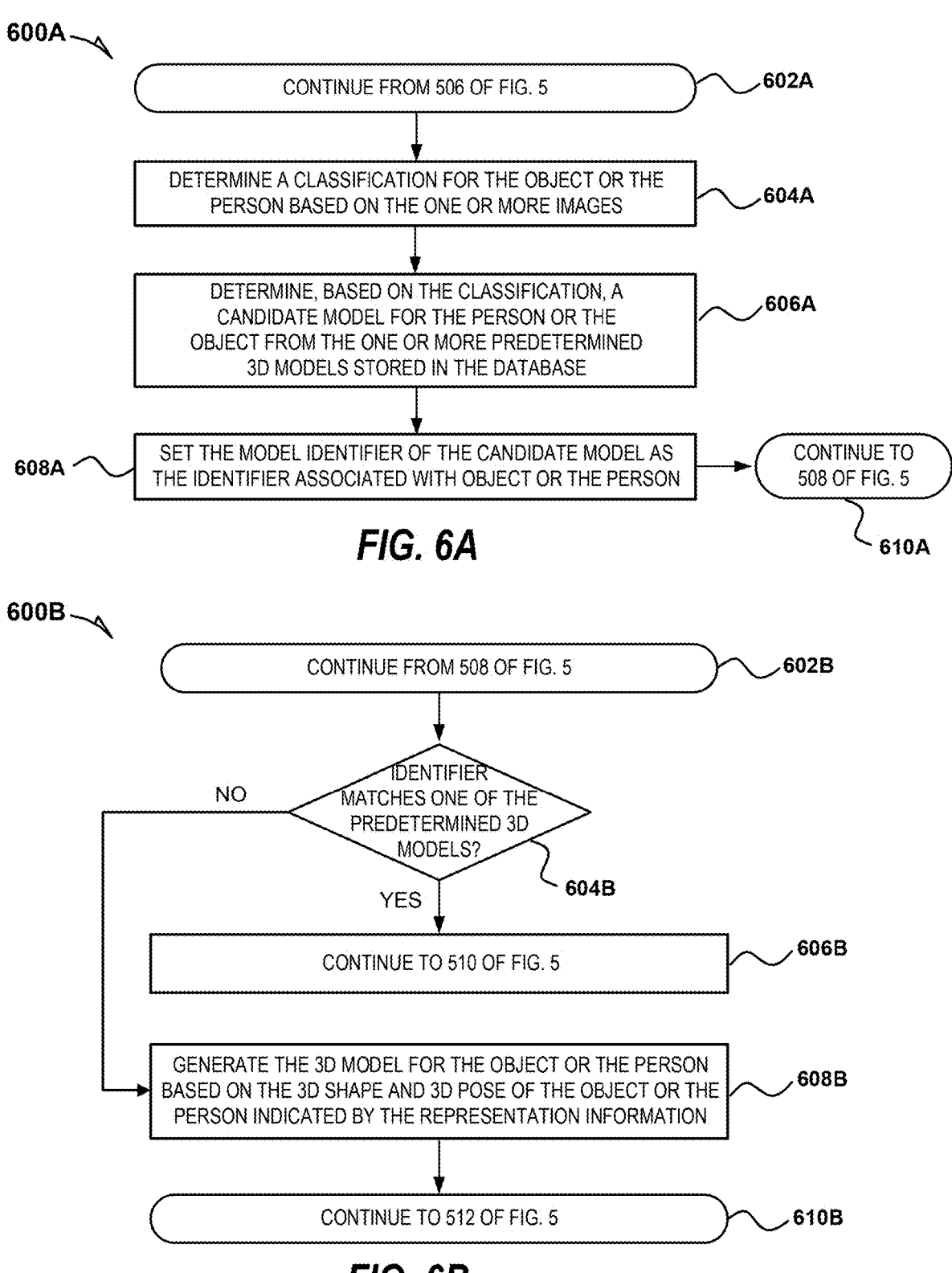
FIG. 6A a flow diagram illustrating an example method that may be performed for determining an identifier for an object or person detected in a medical environment in accordance with one or more embodiments described herein.
FIG. 6B a flow diagram illustrating an example method that may be performed for generating the 3D model for the object or the person based on a 3D shape and a 3D pose of the object or the person in accordance with one or more embodiments described herein.

FIG. 6A a flow diagram illustrating an example method that may be performed for determining an identifier for an object or person detected in a medical environment in accordance with one or more embodiments described herein.

The operations may start at 602A, where the method 600A may continue from operation 506 of method 500 of FIG. 5 as describe above. At operation 604A, a classification for the object (e.g., robotic arm 106) or the person (e.g., patient 118) may be determined based on the one or more input images. For example, the person may be classified as male or female or the object may be classified as medical equipment. At operation 606A, a candidate model for the person or the object from the one or more predetermined 3D models stored in the database (e.g., a 3D CAD model) may be determined based on the classification. At operation 608A, the model identifier of the candidate model may be set as the identifier associated with object or the person. At operation 610A, the method 600A may continue to operation 508 of method 500 of FIG. 5 as describe above.

FIG. 6B a flow diagram illustrating an example method that may be performed for generating the 3D model for the object or the person based on a 3D shape and a 3D pose of the object or the person in accordance with one or more embodiments described herein.

The operations may start at 602B, where the method 600B may continue from operation 508 of method 500 of FIG. 5 as describe above. At operation 604B, it may be determined whether the identifier for the person (e.g., patient 118) or the object (e.g., robotic arm 106) detected in medical environment 100 matches one of the predetermined 3D model stored in a database. Based on the identifier matching a predetermined 3D model stored in the database, at operation 606B, the method 600B may continue to operation 510 of method 500 of FIG. 5 as described above. Based on the identifier not matching a predetermined 3D model stored in the database, at operation 608B, the 3D model for the object or the person may be generated based on the 3D shape and 3D pose of the object or the person as indicated by the representation information. At operation 610B, the method 600B may continue to operation 512 of method 500 of FIG. 5 as describe above.

Figure 7:
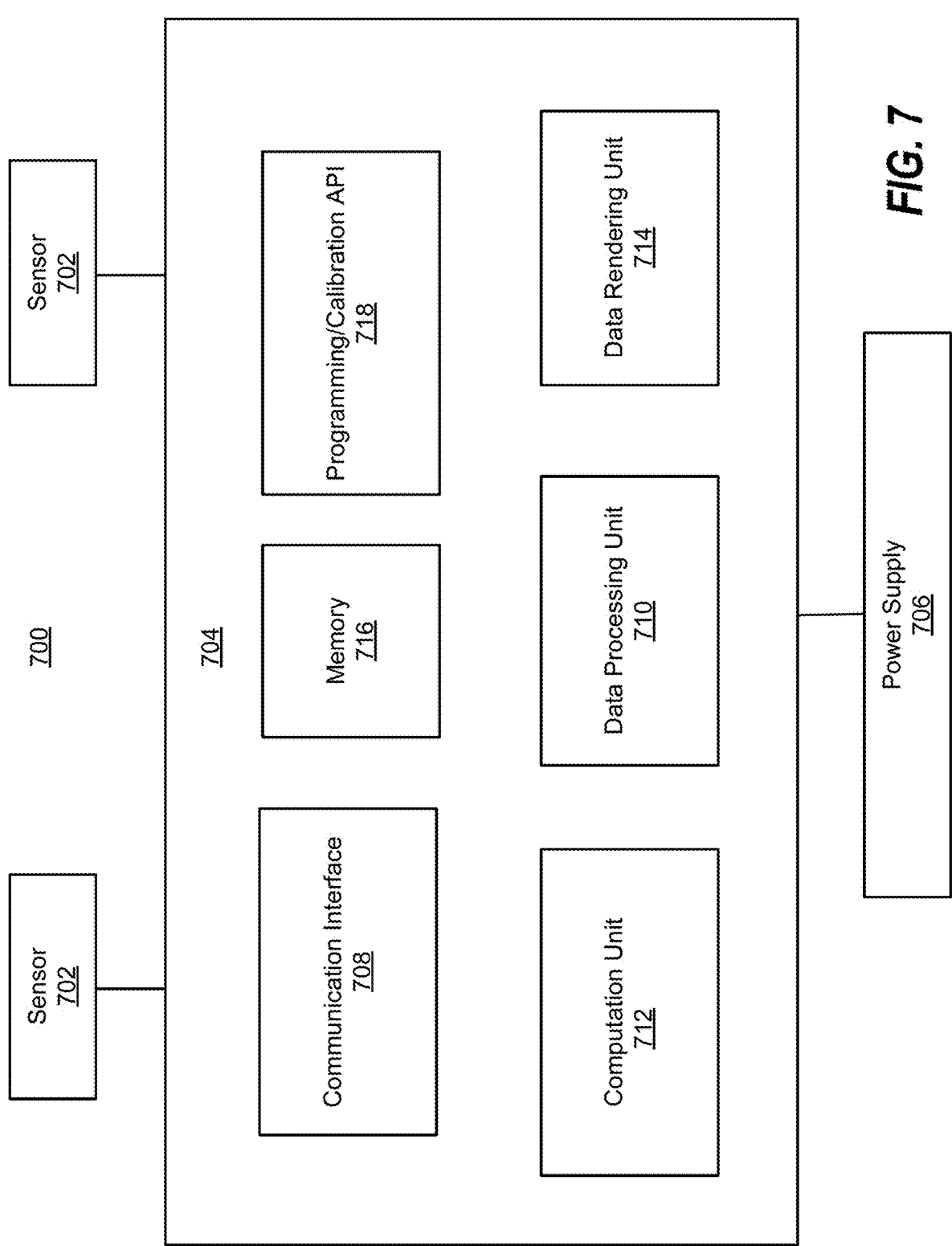
FIG. 7 shows a block diagram illustrating an example of a sensing device in accordance with one or more embodiments described herein.

FIG. 7 illustrates an example sensing device 700 (e.g., the sensing devices 110 shown in FIG. 1) that may be placed or installed in a medical environment (e.g., the medical environment 100 of FIG. 1) to facilitate the visualization of a person (e.g., patient 118) or an object (e.g., robotic arm 106) detected in the medical environment. The sensing device 700 may comprise a sensor 702, a functional unit 704, and/or a power supply 706 that may be configured to be hosted in a housing. Although two sensors are shown in the figure, the sensing device 700 may comprise any number of sensors. Further, although one or more of the components are shown in FIG. 7 as being inside or outside of the functional unit 704, these components may be moved out of or into the functional unit 704 without affecting the functionalities of the sensing device described herein.

As described herein, the sensor 702 may include a RGB sensor, a depth sensor, a RGB plus depth (RGB-D) sensor, a thermo-sensor such as a FIR or NIR sensor, a radar sensor, a motion sensor, a camera (e.g., a digital camera) and/or other types of image capturing circuitry configured to generate images (e.g., 2D images or photos) of a person or an object in the FOV of the sensor. The images generated by the sensor 702 may include, for example, one or more photos, thermal images, and/or radar images of the person or the object. Each of the images may comprise a plurality of pixels that collectively represent a graphic view of the person, object or scene and that may be analyzed to extract features that are representative of one or more characteristics of the person or the object.

The sensor 702 may be communicatively coupled to the functional unit 704, for example, via a wired or wireless communication link. The sensor 702 may be configured to transmit images generated by the sensor to the functional unit 704 (e.g., via a push mechanism) or the functional unit 704 may be configured to retrieve images from the sensor 702 (e.g., via a pull mechanism). The transmission and/or retrieval may be performed on a periodic basis (e.g., based on a preconfigured schedule) or in response to receiving a control signal triggering the transmission or retrieval. The functional unit 704 may be configured to control the operation of the sensor 702. For example, the functional unit 704 may transmit a command to adjust the FOV of the sensor 702 (e.g., by manipulating a direction or orientation of the sensor 702). As another example, the functional unit 704 may transmit a command to change the resolution at which the sensor 702 takes images of a person or an object.

The sensor 702 and/or the functional unit 704 (e.g., one or more components of the functional unit 704) may be powered by the power supply 706, which may comprise an alternative current (AC) power source or a direct current (DC) power source (e.g., a battery power source). When a DC power source such as a battery power source is used, the power supply 706 may be rechargeable, for example, by receiving a charging current from an external source via a wired or wireless connection. For example, the charging current may be received by connecting the sensing device 700 to an AC outlet via a charging cable and/or a charging adaptor (including a USB adaptor). As another example, the charging current may be received wirelessly by placing the sensing device 700 into contact with a charging pad.

The functional unit 704 may comprise one or more of a communication interface circuit 708, a data processing device 710, a computation unit 712, a data rendering unit 714, a memory 716, or a programming and/or calibration application programming interface (API) 718. It should be noted that the components shown in FIG. 7 are provided merely as examples and are not meant to limit the scope of the disclosure. For example, the functional unit 704 is not restricted to including the exact components as shown in FIG. 7. Two or more of the components (e.g., functionalities of the components) may be combined, any one of the components may be divided into sub-components, any one of the components may be omitted, more components may be added, etc. As such, even though the functionalities of the sensing device 700 are described herein as being associated with respective one or more of the components, it will be appreciated that those functionalities may also be performed by a different component and/or be divided among multiple other components.

The functional unit 704 may be configured to receive or retrieve images from the sensor 702 via the communication interface circuit 708, which may include one or more wired and/or wireless network interface cards (NICs) such as ethernet cards, WiFi adaptors, mobile broadband devices (e.g., 4G/LTE/5G cards or chipsets), etc. In examples, a respective NIC may be designated to communicate with a respective sensor. In examples, a same NIC may be designated to communication with multiple sensors.

The images received or retrieved from the sensor 702 may be provided to the data processing device 710, which may be configured to analyze the images and carry out one or more of the operations described herein (e.g., including operations of the processing device 112 described herein). The functionality of the data processing device 710 may be facilitated by the computation unit 712, which may be configured to perform various computation intensive tasks such as feature extraction and/or feature classification based on the images produced by the sensor 702. The computation unit 712 may be configured to implement one or more neural networks such as the one or more CNNs and/or DNNs described herein. The data rendering unit 714 may be configured to generate the one or more visual representations described herein including, e.g., a 3D model of the person or object within a 3D spatial layout of the medical environment, etc.

Each of the data processing device 710, the computation unit 712, or the data rendering unit 714 may comprise one or more processors such as a central processing device (CPU), a graphics processing device (GPU), a microcontroller, a reduced instruction set computer (RISC) processor, an application specific integrated circuit (ASIC), an application-specific instruction-set processor (ASIP), a physics processing device (PPU), a digital signal processor (DSP), a field programmable gate array (FPGA), or a combination thereof. The data processing device 710, computation unit 712, and/or data rendering unit 714 may also comprise other type(s) of circuits or processors capable of executing the functions described herein. Further, the data processing device 710, the computation unit 712, or the data rendering unit 714 may utilize the memory 716 to facilitate one or more of the operations described herein. For example, the memory 716 may include a machine-readable medium configured to store data and/or instructions that, when executed, cause the processing device 710, the computation unit 712, or the data rendering unit 714 to perform one or more of the functions described herein. Examples of a machine-readable medium may include volatile or non-volatile memory including but not limited to semiconductor memory (e.g., electrically programmable read-only memory (EPROM), electrically erasable programmable read-only memory (EE-PROM)), flash memory, and/or the like. And even though not shown in FIG. 7, the sensing device 700 may also comprise one or more mass storage devices that include a magnetic disk such as an internal hard disk, a removable disk, a magneto-optical disk, a CD-ROM or DVD-ROM disk, etc., on which instructions and/or data may be stored to facilitate the performance of the functions described herein.

The operation of the sensing device 700 may be configured and/or controlled through the programming/calibration API 718, for example, using a remote programming device such as the programming device 116 in FIG. 1. In examples, the programming/calibration API 718 may be configured to receive commands (e.g., one or more digital messages) from the programming device that adjust the operating parameters of the sensing device 700 such as the orientation and/or FOV of a sensor, a resolution at which a sensor captures images, a periodicity at which images are received or retrieved from a sensor, etc. In response to receiving a command from the programming device, the sensing device 700 (e.g., the functional unit 704) may adjust one or more aspects of its operation in accordance with the command. For instance, if the command specifies a higher output quality, the sensing device 700 may output a high-resolution image in response, and if the command specifies a higher frame rate, the sensing device 300 may output lower-resolution images at increased frame rates.

The sensing device 700 (e.g., the functional unit 704) may also be configured to receive ad hoc commands through the programming/calibration API 718. Such ad hoc commands may include, for example, a command to zoom in or zoom out a sensor, a command to reset the sensing device 700 (e.g., restart the device or reset one or more operating parameters of the device to default values), a command to enable or disable a specific functionality of the sensing device 700, etc. The sensing device 700 (e.g., the functional unit 704) may also be programmed and/or trained (e.g., over a network) via the programming/calibration API 718. For example, the sensing device 700 may receive training data and/or operating logics through the programming/calibration API 718 during and/or after an initial configuration process.

The sensing device 700 and/or the functional unit 704 may be configured to be modular and extensible such that sensors, communication circuits, data processing devices, computation units, and/or data rendering units may be added to or removed from the sensing device 700, for example, to accommodate different system settings, configurations and/or requirements in a medical environment. For example, if output quality is the priority in the medical environment, a high-resolution sensor (e.g., a high-resolution camera) may be included in (e.g., added to) the sensing device 700 to satisfy the priority. On the other hand, if the priority is on output speed (e.g., frame rate), a sensor (e.g., a camera) with lower resolution and/or a communication circuit with faster bitrates (e.g., an ethernet card rather than a WiFi card) may be used to meet the output requirement. As another example, the sensing device 700 may be configured to work (e.g., simultaneously) with multiple devices in the medical environment such as multiple imaging modalities (e.g., CT, MR, etc.), in which case the sensing device may include respective sets of sensors, communication circuits, power supplies, processors (e.g., data processing devices, computation units, and/or data rendering units as described herein) for the respective medical devices. As yet another example, the sensing device 700 may be configured to receive images of multiple patients (e.g., from different sensors) and generate respective 2D or 3D models for the patients based on the images, for example, simultaneously. In such a scenario, the sensing device 700 may include respective sets of sensors, communication circuits, power supplied, processors (e.g., data processing devices, computation units, and/or data rendering units as described herein) for capturing and processing the respective images of the respective patients.

In examples, the sensing device 700 and/or the functional unit 704 may comprise multiple slots (e.g., expansion boards, etc.) each equipped with at least one of a power connector or a communication circuit (e.g., a network interface card, a USB port, etc.) capable of transmitting and receiving information over a wired or wireless communication link. Sensors and/or processors (e.g., data processing devices, computation units, and/or data rendering units as described herein) may be hosted in (e.g., inserted into) these slots, upon which the sensors and/or processors may receive power through the respective power connectors and perform data exchange with one or more internal or external devices via the respective communication circuits. These sensors and processors may respectively possess similar capabilities as the sensor 702, the data processing device 710, the computation unit 712, and the data rendering unit 714 described herein, and may be added to or removed from the sensing device 700, for example, to accommodate changing conditions and/or requirements in the medical environment in which the sensing device 700 is installed. In this manner, the sensing device 700 may be modular and extensible to handle data processing tasks associated with different patients, devices, and/or imaging modalities. In other example situations such as when the amount of computation, communication, and/or data storage workload approaches or exceeds the capabilities of one set of sensors and/or processors, more of the sensors and/or processors may be added to share the workload.

Figure 8:
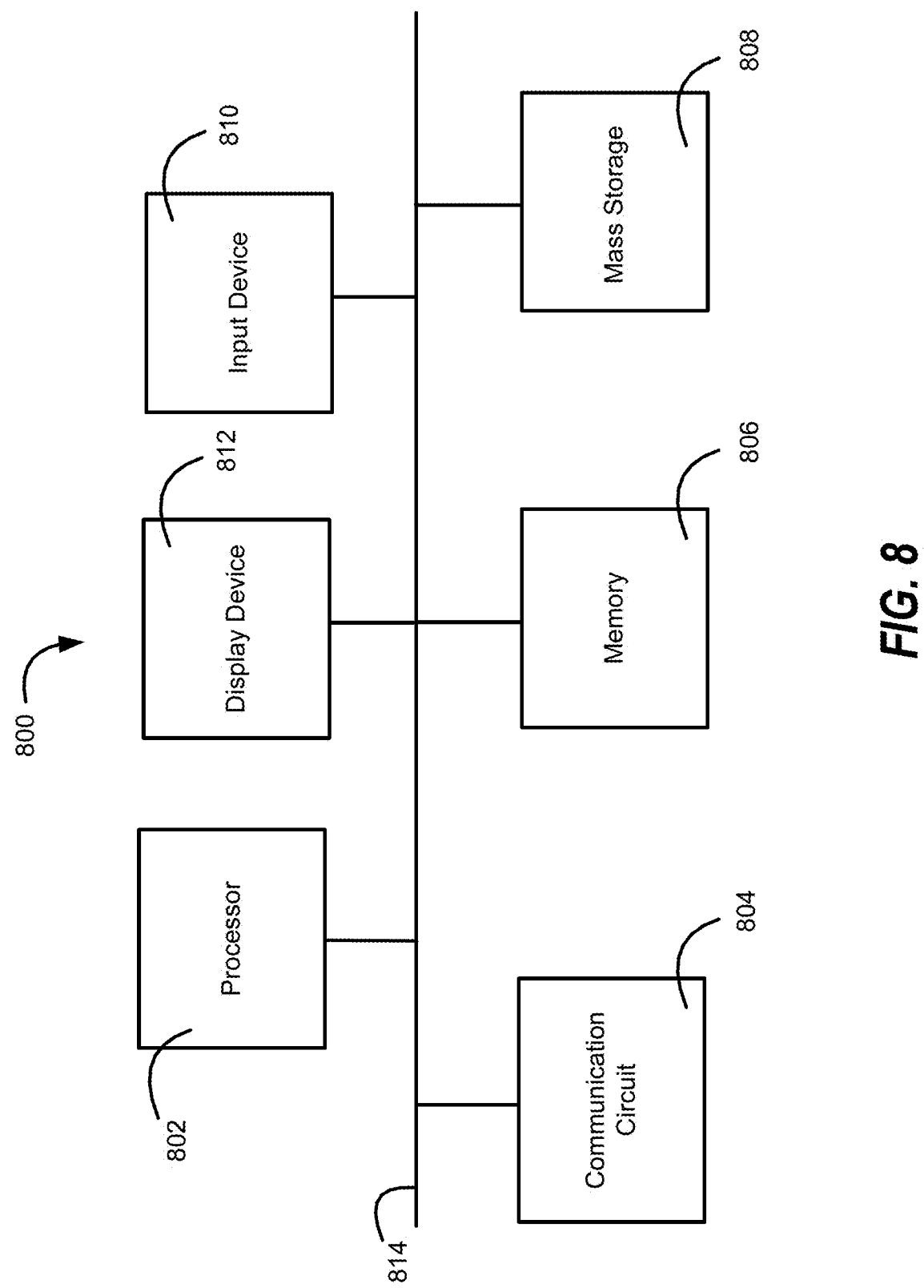
FIG. 8 shows a block diagram illustrating an example of a processing device in accordance with one or more embodiments described herein.

FIG. 8 illustrates example components of a processing device 800 (e.g., the computing device or visualization device of the visualization system described herein) that may be used to perform one or more of the tasks described herein. As shown, the processing device 800 may include a processor 802, which may be a central processing device (CPU), a graphics processing device (GPU), a microcontroller, a reduced instruction set computer (RISC) processor, application specific integrated circuits (ASICs), an application-specific instruction-set processor (ASIP), a physics processing device (PPU), a digital signal processor (DSP), a field programmable gate array (FPGA), or any other circuit or processor capable of executing the functions described herein. The processing device 800 may further include a communication circuit 804, a memory 806, a mass storage device 808, an input device 810, a display device 812, and/or a communication link 814 (e.g., a communication bus) over which the one or more components shown in FIG. 8 may exchange information. The communication circuit 804 may be configured to transmit and receive information utilizing one or more communication protocols (e.g., TCP/IP) and one or more communication networks including a local area network (LAN), a wide area network (WAN), the Internet, a wireless data network (e.g., a Wi-Fi, 3G, 4G/LTE, or 5G network). The memory 806 may include a storage medium configured to store machine-readable instructions that, when executed, cause the processor 802 to perform one or more of the functions described herein. Examples of the machine-readable medium may include volatile or non-volatile memory including but not limited to semiconductor memory (e.g., electrically programmable read-only memory (EPROM), electrically erasable programmable read-only memory (EEPROM)), flash memory, and/or the like. The mass storage device 808 may include one or more magnetic disks such as one or more internal hard disks, one or more removable disks, one or more magneto-optical disks, one or more CD-ROM or DVD-ROM disks, etc., on which instructions and/or data may be stored to facilitate the operation of the processor 802. The input device 810 may include a keyboard, a mouse, a voice-controlled input device, a touch sensitive input device (e.g., a touch screen), and/or the like for receiving user inputs to the processing device 800. The display device 812 may include one or more monitors (e.g., computer monitors. TV monitors, tablets, mobile devices such as smart phones, etc.), one or more speakers, one or more augmented reality (AR) devices (e.g., AR goggles), and/or other accessories configured to facilitate the visual representation of contents on the display device 812. These contents may include, for example, information generated by the processing device such as a 3D model of a patient, simulated movements of a medical device, a plot of radiation exposure over time, etc. The display may be rendered in various formats including, for example, videos, animations, and/or VR/AR presentations.

It should be noted that the processing device 800 may operate as a standalone device or may be connected (e.g., networked or clustered) with other computation devices to perform the functions described herein. And even though only one instance of each component is shown in FIG. 8, a skilled person in the art will understand that the processing device 800 may include multiple instances of one or more of the components shown in the figure. Furthermore, although example operations of the processing device may be depicted and described herein in a specific order, the operations may also take place in other orders, concurrently, and/or with other operations not presented or described herein. Not all operations that the processing device is capable of performing are depicted and described herein, and not all illustrated operations are required to be performed by the processing device.

While this disclosure has been described in terms of certain embodiments and generally associated methods, alterations and permutations of the embodiments and methods will be apparent to those skilled in the art. Accordingly, the above description of example embodiments does not constrain this disclosure. Other changes, substitutions, and alterations are also possible without departing from the spirit and scope of this disclosure. In addition, unless specifically stated otherwise, discussions utilizing terms such as "analyzing." "determining," "enabling." "identifying." "modifying" or the like, refer to the actions and processes of a computer system, or similar electronic computing device, that manipulates and transforms data represented as physical (e.g., electronic) quantities within the computer system's registers and memories into other data represented as physical quantities within the computer system memories or other such information storage, transmission or display devices.

It is to be understood that the above description is intended to be illustrative, and not restrictive. Many other implementations will be apparent to those of skill in the art upon reading and understanding the above description. The scope of the disclosure should, therefore, be determined with reference to the appended claims, along with the full scope of equivalents to which such claims are entitled.

The invention claimed is:

1. A system, comprising:
a computing device, wherein the computing device comprises one or more image sensors and one or more processors, the one or more image sensors configured to capture one or more images of a medical environment, the one or more processors configured to:
identify, based on the one or more images, an object or a person in the medical environment, wherein, as a part of the identification, the computing device is configured to determine at least an identifier associated with the object or the person, a position of the object or the person in the medical environment, and a three-dimensional (3D) shape of the object or the person; and
generate representation information that indicates at least the identifier associated with the object or the person, the position of the object or the person in the medical environment, and the 3D shape of the object or the person; and
a visualization device, wherein the visualization device comprises at least one processor and at least one display device, the at least one processor configured to:
obtain the representation information generated by the computing device;
determine, based on the representation information obtained from the computing device and one or more predetermined 3D models, a 3D model for the object or the person identified in the medical environment; and
generate a visual depiction of at least the object or the person in the medical environment based on the determined 3D model and the position of the object or the person indicated by the representation information;
wherein the one or more predetermined 3D models are associated with respective model identifiers, and wherein the one or more processors of the computing device being configured to determine the identifier associated with the object or the person comprises the one or more processors being configured to:
determine a classification for the object or the person based on the one or more images;
match the classification to a candidate model stored in a database; and
set the model identifier of the candidate model as the identifier of the object or the person.

2. The system of claim 1, wherein the at least one processor of the visualization device being configured to determine the 3D model for the object or the person comprises the at least one processor of the visualization device being configured to determine a candidate 3D model for the object or the person by matching the identifier associated with the object or the person with the model identifier associated with the candidate 3D model.

3. The system of claim 2, wherein the at least one processor of the visualization device being configured to determine the 3D model for the object or the person further comprises the at least one processor of the visualization device being configured to modify the candidate 3D model based at least on the 3D shape of the object or the person indicated by the representation information.

4. The system of claim 3, wherein the one or more processors of the computing device are further configured to determine a 3D pose of the object or the person based on the one or more images, wherein the representation information further indicates the 3D pose of the object or the person, and wherein the at least one processor of the visualization device is configured to modify the candidate 3D model further based on the 3D pose of the object or the person.

5. The system of claim 4, wherein the at least one processor of the visualization device being configured to determine the 3D model for the object or the person identified in the medical environment comprises the at least one processor of the visualization device being configured to determine that none of the one or more predetermined 3D models matches the object or the person and generate the 3D model for the object or the person based on the 3D shape and 3D pose of the object or the person indicated by the representation information.

6. The system of claim 1, wherein the one or more predetermined 3D models include one or more 3D object models associated with a medical device in the medical environment, the one or more predetermined 3D models further including one or more 3D human models associated with a patient or medical personnel in the medical environment.

7. The system of claim 6, wherein the one or more predetermined 3D models include one or more computer-aided design (CAD) models or one or more mesh models.

8. The system of claim 1, wherein the one or more predetermined 3D models are stored in the database and wherein the database is accessible to at least one of the computing device or the visualization device.

9. The system of claim 1, wherein the one or more processors of the computing device being configured to identify the object or the person in the medical environment comprises the one or more processors of the computing device being configured to detect the object or the person in the one or more images based on a machine learning model pre-trained for object or human detection.

10. The system of claim 1, wherein the one or more processors of the computing device being configured to identify the object or the person in the medical environment comprises the one or more processors of the computing device being configured to determine at least the 3D shape of the object or the person based on a machine learning model pre-trained for 3D object or human shape estimation.

11. A method for visualizing a medical environment, the method comprising:

obtaining, at a computing device, one or more images of the medical environment;

identifying, at the computing device, an object or a person in the medical environment based on the one or more images, wherein the identifying comprises determining at least an identifier associated with the object or the person, a position of the object or the person in the medical environment, and a three-dimensional (3D) shape of the object or the person;

generating, at the computing device, representation information that indicates at least the identifier associated with the object or the person, the position of the object or the person in the medical environment, and the 3D shape of the object or the person;

obtaining, at a visualization device, the representation information generated by the computing device;

determining, at the visualization device, a 3D model for the object or the person identified in the medical environment based on the representation information obtained from the computing device and one or more predetermined 3D models; and generating, at the visualization device, a visual depiction of at least the object or the person in the medical environment based on the determined 3D model and the position of the object or the person indicated by the representation information;

wherein the one or more predetermined 3D models are associated with respective model identifiers, and wherein the determining the identifier associated with the object or the person comprises:

determining a classification for the object or the person based on the one or more images;

matching the classification to a candidate model stored in a database; and setting the model identifier of the candidate model as the identifier of the object or the person.

12. The method of claim 11, wherein determining the 3D model for the object or the person comprises:

determining a candidate 3D model for the object or the person by matching the identifier associated with the object or the person with the model identifier associated with the candidate 3D model; and modifying the candidate 3D model based at least on the 3D shape of the object or the person indicated by the representation information to obtain the 3D model for the object or the person.

13. The method of claim 12, further comprising determining, at the computing device, a 3D pose of the object or the person based on the one or more images, wherein the representation information further indicates the 3D pose of the object or the person, and where the 3D model for the object or the person is obtained by modifying the candidate 3D model further based on the 3D pose of the object or the person.

14. The method of claim 13, wherein determining the 3D model for the object or the person identified in the medical environment comprises determining that none of the one or more predetermined 3D models is suitable for the object or the person, and generating the 3D model for the object or the person based at least on the 3D shape and the 3D pose of the object or the person indicated by the representation information.

15. The method of claim 11, wherein the one or more predetermined 3D models include one or more computer-aided design (CAD) object models or mesh object models associated with a medical device in medical environment, the one or more predetermined 3D models further including one or more CAD human models or mesh human models associated with a patient or medical personnel in the medical environment.

16. The method of claim 11, wherein identifying the object or the person in the medical environment comprises detecting the object or the person in the one or more images based on a machine learning model pre-trained for object or human detection.

17. The method of claim 11, wherein identifying the object or the person in the medical environment comprises determining at least the 3D shape of the object or the person based on a machine learning model pre-trained for 3D object or human model estimation.

* * * * *